United States Patent [19]

Lynch

[11] 4,421,937
[45] Dec. 20, 1983

[54] CRYSTAL PURIFICATION

[75] Inventor: Dan K. Lynch, Kirkwood, Mo.

[73] Assignee: Monsanto Company, St. Louis, Mo.

[21] Appl. No.: 336,549

[22] Filed: Jan. 4, 1982

[51] Int. Cl.³ .............................................. C07C 37/84
[52] U.S. Cl. .................................. 568/708; 568/749; 568/755; 585/800; 100/117
[58] Field of Search ....................... 568/708, 755, 749; 585/800; 100/117

[56] References Cited

U.S. PATENT DOCUMENTS 3,113,161  12/1963  Schmalenbach .................... 100/117
3,523,799  4/1970  Rigby .................................. 100/117

Primary Examiner—Werren B. Lone

Attorney, Agent, or Firm—Wendell W. Brooks; Thomas Y. Awalt, Jr.; Arnold H. Cole

[57] ABSTRACT

Mixtures of crystals and a liquid, ordinarily comprising the mother liquor of the crystals are continuously separated by feeding the mixture into a screw type press having drainage apperatures, thereby subjecting the crystals with the mother liquor entrapped therein to pressures sufficient to substantially reduce the interstitial space between crystals. Reduction of the interstitial space causes the mother liquor to be forced out of the drainage aperatures thus purifying the crystals. This achieves a more effective separation of mother liquor from the crystals than can be achieved by gravity or the use of a device such as a centrifuge and eliminates the need for a foreign solvent to wash the mother liquor from the crystals.

5 Claims, 1 Drawing Figure

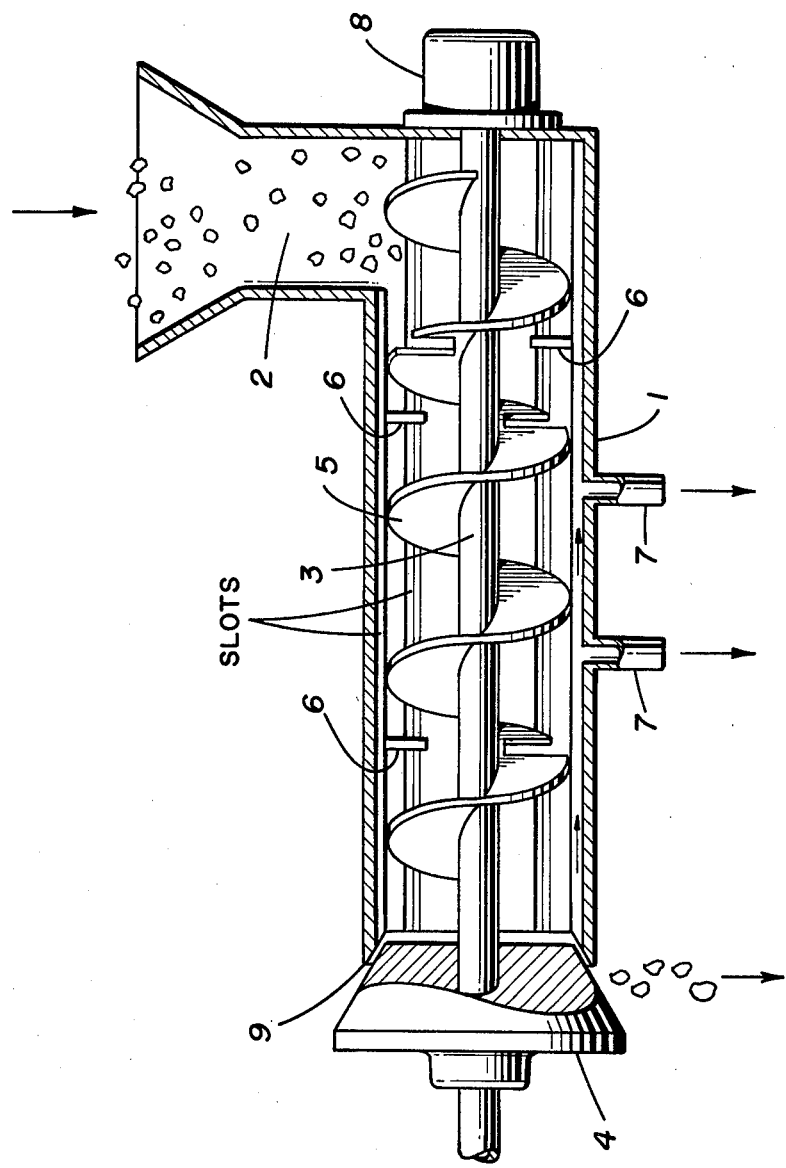

CRYSTAL PURIFICATION

BACKGROUND OF THE INVENTION

A. Field of the Invention

The invention relates to separation and purification, particularly separation of crystals from a mother liquor.

B. Description of the Prior Art

Although a crystal is necessarily pure, in its preparation it will retain some mother liquor when removed from the final magma, and the adhering mother liquor will ordinarily carry impurities. If the adhering mother liquor is not removed, it will contaminate the crystal. In commercial practice, crystals are purified by centrifuging, by filtration and by recrystallization. Residual mother liquor after centrifuging is ordinarily in the range of about 2–5% or more of the weight of crystals. Large uniform crystals from low-viscosity mother liquors will retain a minimum proportion of mother liquor. Non-uniform small crystals from viscous solutions will retain a considerably larger proportion. It is common practice to wash crystals on a centrifuge or filter with a fresh solvent; and the use of counter current washing in multiple stages is known to reduce the loss of crystals by solution in the solvent. The use of a solvent requires separate steps to remove residual solvent from the product such as by drying and some means of solvent recovery. Batch press squeeze purification has been employed commercially but its lack of continuity has been a serious handicap to an otherwise continuous process.

In the commercial production of chemical compounds, particularly aromatic organic compounds, where purification is known to be a problem, any improved method of purifying would be a significant advance in the art and is an object of this invention.

SUMMARY OF THE INVENTION

According to this invention the continuous separation of a feed mixture of crystals and a liquid is provided where the mixture ordinarily comprises about 50–98 weight percent of crystals and about 2–50 weight percent of the liquid. The process comprises continuously feeding the mixture into the screw type press having a feed orifice, a substantially closed compression channel with drainage means and an ejection orifice. The mixture is subjected to a pressure sufficient to substantially reduce interstitial space between crystals while maintaining the crystals at a temperature below their melting point. A substantial portion of the liquid is caused to be drained and removed leaving in the compression channel a purified crystal with compressed interstitial space. The purified crystal is continuously ejected from the closed compression chamber.

In the detailed description, reference will be made to the drawing in which the FIGURE is a schematic section of a screw-type press suitable for the practice of the process of the instant invention.

DETAILED DESCRIPTION OF A PREFERRED EMBODIMENT

Referring now to the drawing, the screw-type press is comprised of barrel 1 with feed orifice 2 and exit orifice 9. Within barrel 1 is continuous screw 5 mounted on screw axle 3. Axle 3 is turned by drive motor 8. Liquid aperatures 7 in conjunction with axal slots 10 are provided for drainage. Within barrel 1 are breaker bars 6 which are spaced intermittently along continuous screw 5. The purpose of the breaker bars is to create discontinuous flow.

In operation, a feed mixture of crystals and the mother liquor are fed into entry orifice 2 and thereafter passed into barrel 1. Continuous screw 5 creates pressure within the barrel which is controlled by adjustable choke 4 so as to regulate the amount of crystals being extruded through exit orifice 9. The liquid in the interstitial spaces is forced out through drainage orifice 7. Drive motor 8 provides the force for turning continuous screw 5 on axle 3.

As stated above, a feed mixture suitable for the practice of this invention employing the particular apparatus described is about 50–99 weight % crystals and about 1–50 weight percent liquid, although of course the only upper limitation on concentration of crystals is that there be sufficient liquid in the press to make separation a justifiable operation and to provide any lubrication necessary for the particular press design in conjunction with the particular crystal composition. If the amount of crystals is less than about 50%, a prior decantation or other separation process step should ordinarily be used so as to make practical the use of the process of this invention. An excess of liquid will ordinarily lower the efficiency and increase the number of pressing cycles required. Of course other screw press designs may efficiently accommodate a higher percentage of liquid. Any type of crystals may be purified in this process. But the practicality of such a process depends on the difficulty of separation. Organic compounds, and especially aromatic organic compounds are often difficult to separate from their solvents. Such compounds as para-dichlorodibenzene, para-nitrochlorobenzene, para-chlorophenol, 2,4-dichlorophenol, stilbene, para-nitrophenol and the like are particularly well suited for the practice of this invention, and for such organic aromatic compounds, a starting concentration of 90–98% by weight of the crystal is preferred in conjunction with the particular apparatus described.

Temperature control, as indicated above, is important because the pressure of and friction created by a screw type press will cause temperatures to rise, often above the melting point of the crystals involved. Control of temperatures of the barrel can be maintained by exposing the outer portion thereof to a cold liquid or gas, by circulation of a cold liquid through cooling coils or circulation channels within the chamber, or by other appropriate means. While it may be desirable to permit a small percentage of crystals to melt during squeeze purification so as to achieve a wash effect, most crystals should not melt; so if temperatures approaching the melting point of the crystals are employed temperatures should be carefully controlled.

By "continuous screw type" or "screw type press" is meant any press in which force is applied continuously or discontinuously to a material within a generally cylindrical chamber from an entry end to an exit end, along a generally spiral path by a turning, continuous screw or discontinuous screw type segment, as against opposing forces created by obstacles along the path of the screw or segments thereof and/or near the exit end of the cylinder. By "generally cylindrical" is meant to include tapered or conical chambers in which the exit end is of a smaller diameter than the entry end as well as cylinders with other than circular cross sections.

Pressures within the screw type press should ordinarily be of the order to about 500–10000 psi ($3447 \times 10^3$–$68947 \times 10^3$ N/m²), with pressures of 5000–6000 psi $34470 \times 10^3$–$41368 \times 10^3$ N/m²) being preferred in the purification of organic aromatic compounds such as those listed above. The pressures applied should be the minimum necessary to achieve the degree of purification needed, and subject to temperature requirements, there is no maximum limitation. Coarse relatively pure crystals will generally require less pressure than fine relatively impure crystals.

EXAMPLE I

A solution of crude nitrochlorobenzene containing small amounts of ortho nitrochlorobenzene, monochlorobenzene, metanitrochlorobenzene (with minor amounts of related compounds) and approximately 90–95% para-nitrochlorobenzene was fed into a screw type press of the type described above operated at 65° C. under 5000–6000 psi ($34470 \times 10^3$–$41368 \times 10^3$ N/m²) pressure. A rich product stream from the screw press contained 99.5% para-nitrochlorobenzene. A lean fraction which was squeezed out through the drainage apertures contained 75–80% para-nitrochlorobenzene.

EXAMPLE II

Crude nitrochlorobenzene containing approximately 70% para-nitrochlorobenzene was fed into a flaker operated at 25°–30° C. The flakes were conveyed first to a screw type press of the type and under conditions described above. Out of the drainage apertures of the screw type press came a lean para-nitrochlorobenzene fraction containing approximately 40% para-nitrochlorobenzene, and this fraction was subsequently distilled and reintroduced into the first screw type press. A second rich fraction was emitted through exit orifice 9. The fraction contained 90–95% para-nitrochlorobenzene, and it was fed into a second screw press which was operated at a temperature of about 65° C. A rich product stream from the second screw press contained at 99.5% para-nitrochlorobenzene. A lean fraction contained 75–80% para-nitrochlorobenzene. This lean stream was recycled to the flaker, and the rich stream was recovered as the product.

EXAMPLE III

A 90% orthonitrochlorobenzene feed was fed into a flaker and thereafter to a continuous screw press of the same type as used in previous examples operated at 25° C. In the screw press, the feed was separated into a 99.0 orthonitrochlorobenzene product and an 80% orthonitrochlorobenzene residue. The product from the first stage was fed directly into another screw press operated at 30°–31° C. The second press separated the feed into a 99.9% orthonitrochlorobenzene component and a 97.0 orthonitrochlorobenzene residue.

EXAMPLE IV t-stilbene was melted and flaked at 25° C. The flaked sample containing about 64% t-stilbene was fed to a continuous screw press operated at 50° C. The product from the first stage (about 80% t-stilbene) was directly fed to another screw press operated at 100° C. The product of the second press was about 98% pure.

I claim:

1. A process for the continuous separation of a feed mixture of 50–99 weight percent crystals of aromatic organic compounds selected from the group consisting of para-dichlorobenzene, para-nitrochlorobenzene, para-chlorophenol, 2,4-dichlorophenol, ortho-nitrophenol, para-nitrophenol, and trans-stilbene and 1–50 weight percent liquid comprising continuously feeding the mixture into a screw type press having a feed orifice, a substantially closed compression channel having drainage means and an ejection orifice, thereby subjecting the mixture to a pressure sufficient to substantially reduce interstitial space between crystals while maintaining the crystals at a temperature below their melting point, causing drainage and removal of a substantial portion of the liquid and leaving in the compression channel purified crystals with compressed interstitial space; and continuously ejecting the purified crystals.

2. The process of claim 1 wherein the feed mixture has a starting concentration of 90–98 percent by weight of crystals.

3. The process of claim 1 where the pressure sufficient to substantially reduce interstitial space between crystals is about 500–10,000 psig ($3447 \times 10^3$–$68947 \times 10^3$ N/m²).

4. The process of claim 2 where the crystals are selected from the group consisting of paradichlorobenzene, para-nitrochlorobenzene, para-chlorophenol, 2-4-di-chlorophenol, orthonitrophenol, paranitrophenol and stilbene and the feed mixture has a starting concentration of 90–98% by weight of crystals.

5. The process of claim 4 where the pressure sufficient to substantially reduce interstitial space between crystals is about 5000–6000 psi ($34470 \times 10^3$–$41368 \times 10^3$ N/m²).

* * * * *